(12) United States Patent
Chen et al.

(10) Patent No.: US 11,995,913 B2
(45) Date of Patent: *May 28, 2024

(54) BODY TEMPERATURE MONITORING DEVICE AND WEARABLE ACCESSARY FOR MEASURING BASAL BODY TEMPERATURE

(71) Applicant: PixArt Imaging Inc., Hsin-Chu County (TW)

(72) Inventors: Nien-Tse Chen, Hsin-Chu County (TW); Yi-Hsien Ko, Hsin-Chu County (TW); Yen-Min Chang, Hsin-Chu County (TW)

(*) Notice: Subject to any disclaimer, the term of this patent is extended or adjusted under 35 U.S.C. 154(b) by 0 days.

This patent is subject to a terminal disclaimer.

(21) Appl. No.: 18/132,423

(22) Filed: Apr. 10, 2023

(65) Prior Publication Data

US 2023/0252819 A1    Aug. 10, 2023

Related U.S. Application Data

(60) Continuation of application No. 17/470,298, filed on Sep. 9, 2021, now Pat. No. 11,657,646, which is a
(Continued)

(51) Int. Cl.
| | |
|---|---|
| *G06K 9/00* | (2022.01) |
| *A61B 5/00* | (2006.01) |
| *A61B 5/01* | (2006.01) |
| *G01J 5/00* | (2022.01) |
| *G01J 5/02* | (2022.01) |

(Continued)

(52) U.S. Cl.
CPC .......... *G06V 40/161* (2022.01); *A61B 5/0008* (2013.01); *A61B 5/01* (2013.01); *A61B 5/742* (2013.01); *A61B 5/746* (2013.01); *G01J 5/0025* (2013.01); *G01J 5/026* (2013.01); *G06F 18/22* (2023.01); *G06F 18/251* (2023.01); *G06F 21/32* (2013.01); *G06V 10/143* (2022.01); *G06V 10/761* (2022.01); *G06V 10/803* (2022.01); *G06V 40/113* (2022.01); *G06V 40/168* (2022.01); *G06V 40/172* (2022.01);
(Continued)

(58) Field of Classification Search
None
See application file for complete search history.

(56) References Cited

U.S. PATENT DOCUMENTS 8,233,047 B2    7/2012    Shimbo et al.
9,603,566 B2 *  3/2017    Chen ................... A61B 5/4812
(Continued)

FOREIGN PATENT DOCUMENTS

CN    109377628 A    2/2019

OTHER PUBLICATIONS

Renevey et al., "Photoplethysmography-Based Bracelet for Automatic Sleep Stages Classification: Preliminary Results", IASTED 2014, Zurich, Switzerland (Year: 2014).*
(Continued)

*Primary Examiner* — Feng Niu
(74) *Attorney, Agent, or Firm* — Bruce Stone LLP; Joseph A. Bruce

(57)    ABSTRACT

There is provided a recognition system adaptable to a portable device or a wearable device. The recognition system senses a body heat using a thermal sensor, and performs functions such as the living body recognition, image denoising and body temperature prompting according to detected results.

16 Claims, 5 Drawing Sheets

Related U.S. Application Data division of application No. 16/442,783, filed on Jun. 17, 2019, now Pat. No. 11,328,152.

(51) Int. Cl.

| | | |
|---|---|---|
| *G06F 18/22* | (2023.01) | |
| *G06F 18/25* | (2023.01) | |
| *G06F 21/32* | (2013.01) | |
| *G06V 10/143* | (2022.01) | |
| *G06V 10/74* | (2022.01) | |
| *G06V 10/80* | (2022.01) | |
| *G06V 40/10* | (2022.01) | |
| *G06V 40/16* | (2022.01) | |
| *G06V 40/20* | (2022.01) | |
| *G06V 40/40* | (2022.01) | |
| *G16H 40/63* | (2018.01) | |

(52) U.S. Cl.
CPC .............. *G06V 40/20* (2022.01); *G06V 40/28* (2022.01); *G06V 40/45* (2022.01); *G16H 40/63* (2018.01); *G01J 2005/0077* (2013.01); *G06V 40/117* (2022.01); *G06V 40/16* (2022.01)

(56) References Cited

U.S. PATENT DOCUMENTS

| | | |
|---|---|---|
| 10,029,047 B2 | 7/2018 | Gupta et al. |
| 10,691,943 B1 | 6/2020 | Ferstl et al. |
| 11,157,605 B2 | 10/2021 | Guo et al. |
| 11,615,642 B2 | 3/2023 | Chen et al. |
| 11,615,871 B2 | 3/2023 | Gupta et al. |
| 2013/0281883 A1* | 10/2013 | Nishida ................. A61B 5/742 600/586 |
| 2016/0081615 A1* | 3/2016 | Chen .................... A61B 5/4812 340/575 |
| 2021/0397817 A1 | 12/2021 | Su et al. |
| 2021/0401291 A1 | 12/2021 | Schriek et al. |

OTHER PUBLICATIONS

Marrin et al., "A meta-analytic approach to quantify the dose-response relationship between melatonin and core temperature." European Journal of Applied Physiology 113(2013): 2323-2329. (Year: 2013).

\* cited by examiner

BODY TEMPERATURE MONITORING DEVICE AND WEARABLE ACCESSARY FOR MEASURING BASAL BODY TEMPERATURE

CROSS REFERENCE TO RELATED APPLICATION

The present application is a continuation application of U.S. application Ser. No. 17/470,298, filed on Sep. 9, 2021, which is a divisional application of U.S. application Ser. No. 16/442,783, filed on Jun. 17, 2019, the disclosures of which are hereby incorporated by reference herein in their entirety.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

BACKGROUND

1. Field of the Disclosure

This disclosure generally relates to a recognition system and device and, more particularly, to a recognition system and device that use a thermal sensor to implement functions including the living body recognition, image denoising and body temperature monitoring.

2. Description of the Related Art

The image sensor has been broadly adapted to portable devices as an unlocking means. However, it is difficult to directly use an image sensor to identify a living body in some scenarios, and the image sensor further has a problem of being easily affected by ambient light. In order to solve these issues, a complicated algorithm generally has to be used.

In addition, due to the population aging, the burden for elder and infant nursing to the society gradually becomes heavier. It is not possible to fully rely on human to do the nursing since there is no longer enough manpower, the technology must be used to implement the automatic monitoring thereby reducing the manpower requirement and society cost.

Accordingly, the present disclosure provides a recognition system that adopts a temperature sensor to compensate the insufficiency of a system that uses only an image sensor.

SUMMARY

The present disclosure provides a face recognition system capable of performing the living body recognition.

The present disclosure further provides a gesture recognition system capable of eliminating the ambient light interference.

The present disclosure further provides a medical monitoring system for the medical care system such as a hospital or nursing home.

The present disclosure further provides a body temperature monitoring device for the home care.

The present disclosure provides a body temperature monitoring device including a wearable accessory, a thermal sensor, an acceleration detection device, a display and a processor. The wearable accessory is configured to be worn on a human body. The thermal sensor is in the wearable accessory, and configured to measure a basal body temperature of the human body. The acceleration detection device is in the wearable accessory, and configured to output an acceleration value. The display is on the wearable accessory, and configured to prompt an ovulatory phase. The processor is in the wearable accessory, and configured to identify a wake up time of the human body based on the acceleration value, control the thermal sensor to measure the basal body temperature at the wake up time, record the basal body temperature measured every day, and control the display to prompt the ovulatory phase when a temperature variation of the basal body temperature exceeds a temperature variation threshold.

The present disclosure further provides a warble accessary including a thermal sensor, an acceleration detection device and a processor. The thermal sensor is configured to measure a basal body temperature via a skin surface of a human body. The acceleration detection device is configured to output an acceleration value. The processor is coupled to the thermal sensor and the acceleration detection device, and configured to identify a wake up time of the human body based on the acceleration value, control the thermal sensor to measure the basal body temperature at the wake up time, record the basal body temperature measured every day, and give a hint when a temperature variation of the basal body temperature exceeds a temperature variation threshold.

The present disclosure further provides a warble accessary including a thermal sensor, a display, an acceleration detection device and a processor. The thermal sensor is configured to measure a basal body temperature via a skin surface of a user when the user wakes up every day. The acceleration detection device is configured to output an acceleration value. The processor is coupled to the thermal sensor, the display and the acceleration detection device, and configured to identify a wake up time of the user every day based on the acceleration value, control the thermal sensor to measure the basal body temperature at the wake up time every day, and control the display to give a hint when a temperature variation of the basal body temperature measured every day exceeds a temperature variation threshold.

In one aspect, the body temperature monitoring device further includes a physiological detection device configured to detect a PPG signal such that the body temperature monitoring device identifies a wake up time according to the PPG signal, and controls the thermal sensor to automatically measure the basal body temperature at the wake up time.

The face recognition system and the gesture recognition system of the present disclosure can be applied to a same portable device. For example, the face recognition system is used as an unlocking device, and the gesture recognition system is used for device operation. Accordingly, the recognition system firstly activates or turns on the face recognition function, and the gesture recognition function is activated or turned on after a registered face is recognized.

In the present disclosure, the denoising method of the gesture recognition system is also adaptable to the face recognition system to improve the recognition accuracy of the system.

In the present disclosure, the body temperature monitoring device is also adaptable to the medical monitoring system. For example, a same wearable device executes different functions such as the fever monitoring or basal body temperature monitoring by selecting different operating modes.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

It should be noted that, wherever possible, the same reference numbers will be used throughout the drawings to refer to the same or like parts.

Figure 1:
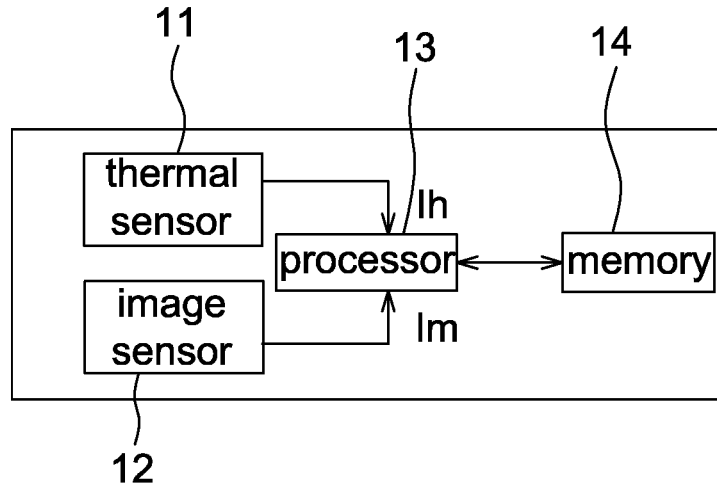
FIG. 1 is a block diagram of a recognition system according to one embodiment of the present disclosure.

Referring to FIG. 1, it is a schematic block diagram of a recognition system 100 according to one embodiment of the present disclosure. The recognition system 100 is applicable to a portable device including electronic devices such as a cell phone, a tablet computer, a notebook computer or the like; and the recognition system 100 is also applicable to a wearable device including electronic devices such as a watch, a bracelet, an armband or the like, but not limited thereto. The recognition system 100 includes a thermal sensor 11, an image sensor 12, a processor 13 and a memory 14. The recognition system 100 performs at least the face recognition and the gesture recognition.

The thermal sensor 11 includes a Pyroelectric Infrared (PIR) type, a thermopile type or a bolometer type sensor, which is used to detect infrared light and output electrical signals (e.g., voltage or current signals) or digital signals to respond to detected temperatures. Preferably, the thermal sensor 11 outputs a two-dimensional thermal image to correspond to a two-dimensional (2D) image frame acquired by the image sensor 12. For example, a detected value of each pixel of the 2D thermal image indicates a temperature of a detected region, and the detected regions corresponding to adjacent pixels of the 2D thermal image are arranged to overlap partially or not overlapped with each other depending on the microlens arrangement thereupon.

Compared with the conventional temperature sensor that performs the thermal sensing or temperature sensing by contacting the object to be detected, the thermal sensor 11 of the present disclosure is capable of detecting the temperature by non-contacting with the object to be detected because the thermal sensor 11 can be a thermopile sensor or a bolometer sensor. In other words, the thermal sensor 11 of the present disclosure can detect the temperature of a target (e.g., human body) even though the target is covered by clothes or cloth thereby having higher reliability and applicability.

The image sensor 12 includes, for example, a CCD image sensor, a CMOS image sensor or the like, which has multiple pixels arranged in a matrix to output the 2D image frame.

The processor 13 is, for example, a digital signal processor (DSP), a microcontroller (MCU), a central processing unit (CPU), an application specific integrated circuit (ASIC), a graphic processing unit (GPU) or the like. The processor 13 is electrically coupled to the thermal sensor 11 and the image sensor 12 to respectively receive a thermal image Ih and an image frame Im for the post-processing by software and/or hardware. The processor 13 also controls ON/OFF of the thermal sensor 11 and the image sensor 12 as well as operation of pixels thereof.

The memory 14 includes, for example, a volatile memory and/or non-volatile memory. The memory 14 is used to previously record the algorithm, threshold(s) and parameter(s) used by the processor 13 in the post-processing. In different applications, the memory 14 further temporarily stores data of the thermal image Ih and/or the image frame Im detected during operation.

Figure 2A:
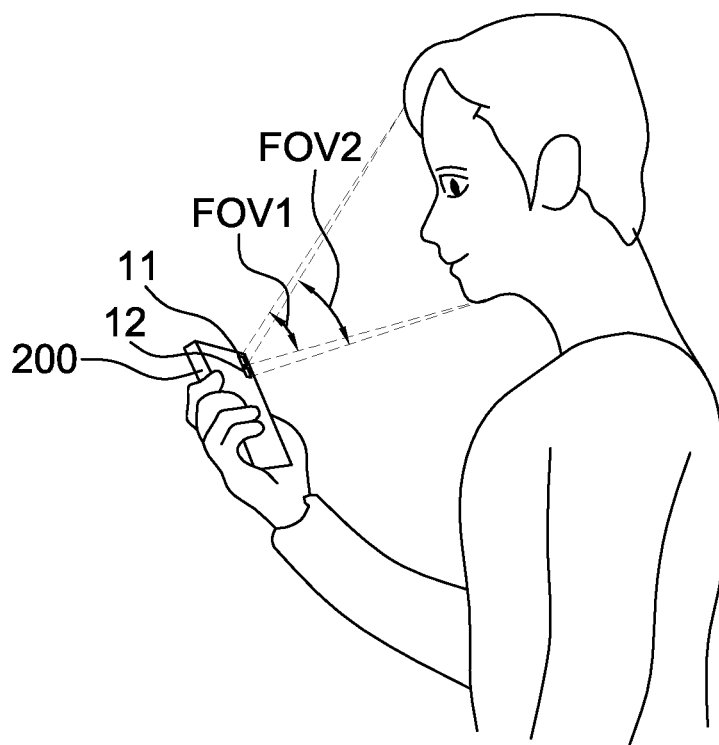
FIG. 2A is an operational schematic diagram of a face recognition system according to a first embodiment of the present disclosure.
Figure 2B:
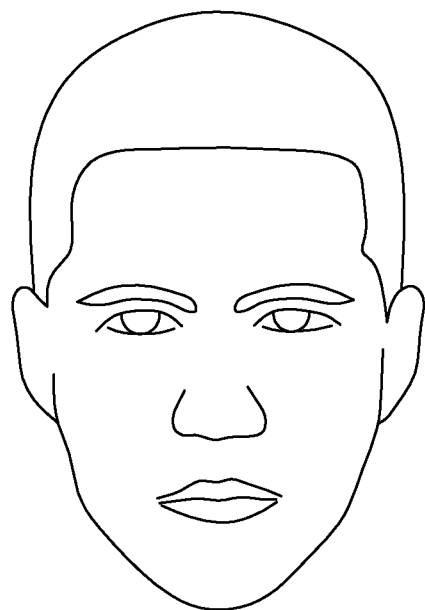
FIG. 2B is a schematic diagram of a face image acquired by a face recognition system according to a first embodiment of the present disclosure.
Figure 2C:
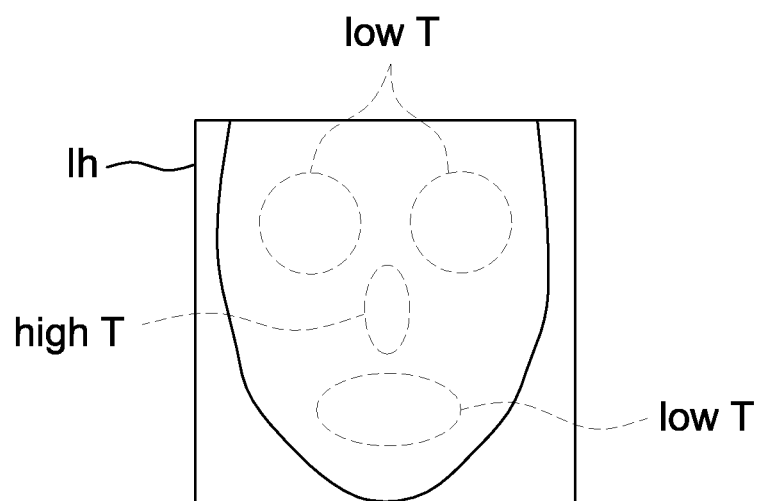
FIG. 2C is a schematic diagram of a temperature distribution of a thermal image acquired by a face recognition system according to a first embodiment of the present disclosure.

Referring to FIG. 2A, it is a schematic diagram of a face recognition system 200 according to a first embodiment of the present disclosure. FIG. 2A shows the face recognition system 200 being arranged close to the side of a portable device facing the user. The face recognition system 200 includes the thermal sensor 11, the image sensor 12, the processor 13 and the memory 14 shown in FIG. 1. The thermal sensor 11 acquires a thermal image Ih (e.g., FIG. 2C showing the temperature distribution thereof) with a first field of view FOV1, and the thermal image Ih is outputted to the processor 13. The image sensor 12 acquires an image frame Im (e.g., FIG. 2B showing a face image therein) with a second field of view FOV2, and the image frame Im is outputted to the processor 13. To acquire corresponding features, at least a part of FOV1 overlaps with FOV2 to acquire information of the same area or surface using different sensors. The thermal sensor 11 and the image sensor 12 are arranged to simultaneously or alternatively acquire images without particular limitations.

The processor 13 performs the face recognition and/or the material recognition according to the image frame Im, wherein the processor 13 uses the conventional face recognition algorithm to recognize facial features of a face image (e.g., as shown in FIG. 2B), and uses the conventional material recognition algorithm to recognize skin material in the image frame Im. The processor 13 performs the living body recognition according to a regional heat distribution in the thermal image Ih corresponding to the facial features of the face image in the image frame Im.

In an image type unlocking system, to prevent an unregistered person from unlocking the system using a photo or video of a registered face, the face recognition system 200 of the first embodiment of the present disclosure distinguishes a fake according to the thermal image Ih captured by the thermal sensor 11 and the skin material of a face in the image frame Im. Accordingly, the living body herein is referred to a real person instead of a photo or video.

For example in one non-limiting aspect, the processor 13 does not turn on the thermal sensor 11 before identifying that a registered face image is contained in the image frame Im or the registered face image has skin material so as to reduce the power consumption, i.e. the processor 13 turning on the thermal sensor 11 only when a registered face image is identified in the image frame Im or the registered face image has skin material, but the present disclosure is not limited thereto.

In another non-limiting aspect, the processor 13 conversely controls the thermal sensor 11 and the image sensor 12. That is, the processor 13 does not turn on the image sensor 12 before an area of an object image in the thermal image Ih is identified to be larger than a threshold. The processor 13 turns on the image sensor 12 to perform the face recognition only when the thermal image Ih contains a valid face image (i.e. object area larger than the threshold). In other aspects, during the unlocking, the thermal sensor 11 and the image sensor 12 are both turned on or activated.

In the first embodiment, a range covered by a first field of view FOV1 of the thermal sensor 11 is preferably larger than a second field of view FOV2 of the image sensor 12. In addition, as the living body recognition is performed according to the thermal image Ih, the processor 13 only performs the 2D face recognition according to the image frame Im without performing the three-dimensional (3D) face recognition to reduce the power computation. Traditionally, the 3D face recognition can be used to distinguish a photo from a person, but higher calculation loading is required.

In addition, to further prevent an unregistered person to perform the unlocking using a heated photo, the processor 13 not only confirms whether an object image in the thermal image Ih has a temperature larger than a predetermined temperature, but also identifies a regional heat distribution in the thermal image Ih. For example referring to FIG. 2C, the thermal image Ih contains high and low temperature regions, e.g., a high temperature region corresponding to a nose area of the face image (as shown in FIG. 2B) in the image frame Im, and low temperature regions corresponding to eyes and mouth areas of the face image in the image frame Im.

In this case, the memory 14 previously records the temperature distribution of various face regions, which is stored in the memory 14 by detecting a registered user in a setting mode (e.g., entered by executing an application or pressing a key), or obtained by a statistical result which is stored in the memory 14 before shipment. The processor 13 compares (e.g., calculating similarity or correlation) the regional heat distribution in a current thermal image (e.g., a thermal image Ih acquired during the unlocking) with the pre-stored temperature distribution to perform the living body recognition. In addition, the processor 13 calculates a temperature difference between areas of the high and low temperature regions to confirm that an object currently being detected by the face recognition system 200 is indeed a human body rather than a fake.

In another aspect, the processor 13 compares the regional heat distribution in a current thermal image with locations of facial features (e.g., the eyes, nose and mouth) identified from the captured image frame Im to confirm whether the regional heat distribution matches with the corresponding facial features or not. In this way, it is also possible to distinguish a fake from a real human face without recording the temperature distribution previously in the memory 14.

After the confirmation of a registered face is accomplished through the face recognition, the processor 13 then turns on or activates operating functions of an electronic device that adopts the face recognition system 200, e.g., activating the di splay screen.

Figure 3A:
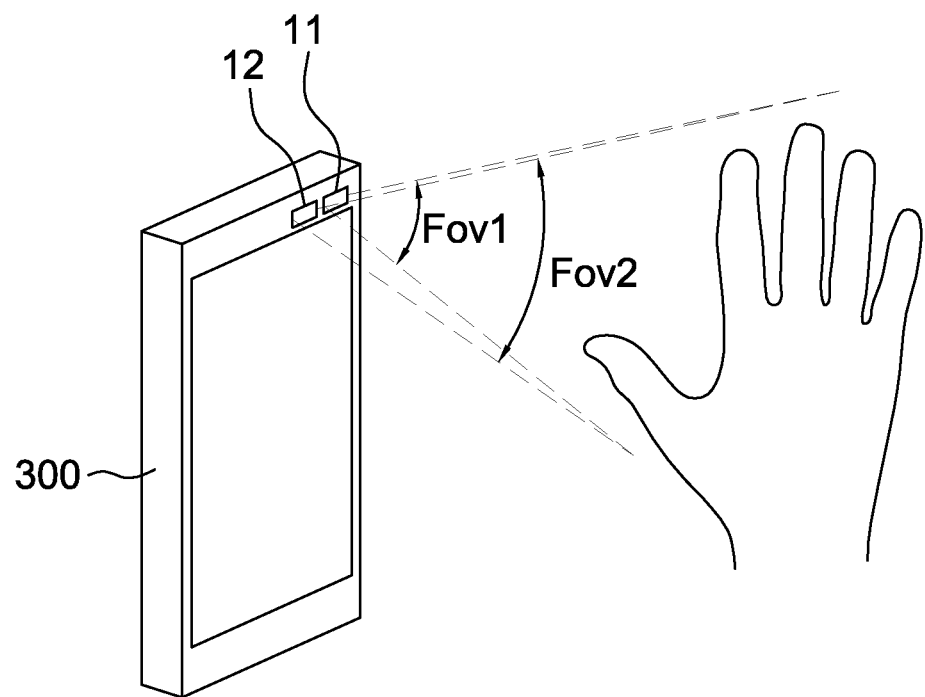
FIG. 3A is an operational schematic diagram of a gesture recognition system according to a second embodiment of the present disclosure.
Figure 3B:
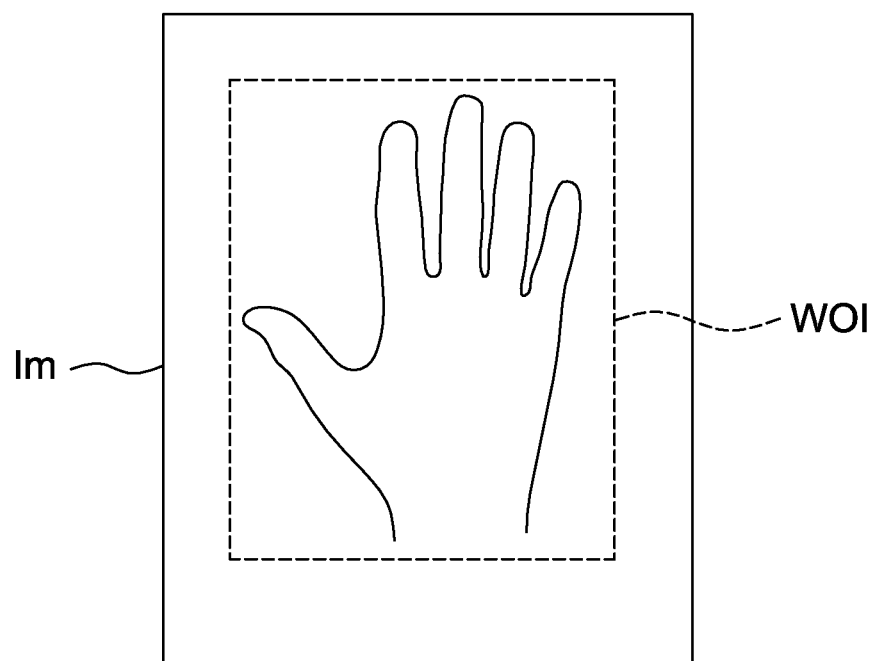
FIG. 3B is a schematic diagram of an image frame acquired by a gesture recognition system according to a second embodiment of the present disclosure.

Referring to FIG. 3A, it is a schematic diagram of a gesture recognition system 300 according to a second embodiment of the present disclosure. FIG. 3A shows the gesture recognition system 300 being arranged at the side of a portable device facing the user. The gesture recognition system 300 also includes the thermal sensor 11, the image sensor 12, the processor 13 and the memory 14 shown in FIG. 1. The thermal sensor 11 is used to acquire a thermal image Ih with a first field of view FOV1, and the thermal image Ih is outputted to the processor 13. The image sensor 12 is used to acquire an image frame Im (as shown in FIG. 3B) with a second field of view FOV2, and the image frame Im is also outputted to the processor 13.

The processor 13 determines a processed region WOI in the thermal image Ih, and performs the gesture recognition according to an image region in the image frame Im corresponding to the processed region WOI determined in the thermal image Ih so as to eliminate the interference from ambient light. Accordingly, to allow the processor 13 to be able to correctly determine the processed region WOI in the image frame Im, in the second embodiment the first field of view FOV1 of the thermal sensor 11 is preferable equal to the second field of view FOV2 of the image sensor 12, and sizes of the thermal image Ih and the image frame Im are preferable identical. For example, a corresponding processed region WOI in the image frame Im is obtained according to pixel addresses or pixel locations within the determined processed region WOI in the thermal image Ih.

For example, the processor 13 identifies a region in the thermal image Ih having a temperature larger than a temperature threshold (determined according to body temperature) as the processed region WOI, which is an image region in the thermal image Ih. As the second field of view FOV2 is arranged corresponding to the first field of view FOV1, the processor 13 confirms a corresponding processed region WOI in the image frame Im as shown in FIG. 3B, wherein a size of the corresponding processed region WOI is smaller than that of the image frame Im. It should be mentioned that the processed range WOI is not limited to a rectangle as shown in FIG. 3B but is another suitable shape as long as it covers the object region in the image frame Im. In some scenarios, two processed regions WOI are defined corresponding to two object regions.

In other aspects, the first field of view FOV1 and the second field of view FOV2 are not totally identical to each other and have an angle difference. In this case, the memory 14 previously stores a space conversion algorithm or matrix transformation algorithm between the thermal image Ih and the image frame Im. In this way, after confirming the processed region WOI in the thermal image Ih, the processor 13 confirms a corresponding processed region WOI in the image frame Im according to the stored algorithm.

In another non-limiting aspect, the processor 13 firstly identifies an object image in the image frame Im, which may also contain an image of ambient light. The processor 13 then removes the non-human image based on the thermal image Ih. For example, the object image outside the processed region WOI is not used in the gesture recognition so as to effectively improve the recognition accuracy and eliminate the interference.

More specifically, in the second embodiment, the processor 13 performs the gesture recognition according to a partial image of the image frame Im, and the thermal image Ih is for the denoising function.

In addition, in the low power consumption scenario, the processor 13 turns on the image sensor 12 only after identifying a processed region WOI in the thermal image Ih larger than a predetermined size. In this case, a whole sensor array of the image sensor 12 is turned on or a part of the sensor array corresponding to the WOI is turned on. In other words, when the thermal image Ih does not contain a region having a temperature higher than a predetermined temperature threshold, the processor 13 only turns on the thermal sensor 11 to capture thermal images Ih at a predetermined frequency; or, even though the thermal image Ih contains a region having a temperature higher than the predetermined temperature threshold, the processor 13 still only turns on the thermal sensor 11 to acquire thermal images Ih at a predetermined frequency if the region is smaller than a predetermined size, which is determined according to a hand size within a detectable distance of the system, but the present disclosure is not limited thereto.

In other aspects, during the gesture recognition, the thermal sensor 11 and the image sensor 12 are both turned on or activated. For example, only a part of pixels of the thermal sensor 11 are turned on, and said the part of pixels corresponds to a pixel region of the image sensor 12 detecting an object. More specifically, in the present disclosure sensor arrays of the thermal sensor 11 and the image sensor 12 are not necessary to be fully turned on but only a part of pixels thereof are turned on to reduce the power consumption.

In an alternative embodiment, the processor 13 performs a material recognition in the image frame Im captured by the image sensor 11 at first and then performs the gesture recognition according to the thermal image Ih captured by the thermal sensor 11. For example, if an object image in the image frame Im is not identified to have skin material by the processor 13, the thermal sensor 11 is not turned on. The thermal sensor 11 is turned on only when a skin material is identified in the image frame Im. Furthermore, the processor 13 also determines a WOI in the thermal image Ih based on a skin material region in the image frame Im, i.e., the processor 13 firstly determining a skin material region in the image frame Im at first and then determining a WOI in the thermal image Ih corresponding to the skin material region. The gesture recognition is performed using the object image only within the WOI in the thermal image Ih.

It should be mentioned that although in the above first and second embodiments the recognition system 100 is illustrated by applying to a portable device, the present disclosure is not limited thereto. The recognition system 100 of the first and second embodiments is also applicable to a wearable device, the security system and/or control system of a gate or a vehicle. The processor 13 performs the living body recognition and denoising using the thermal image Ih to improve the identification accuracy and security.

Figure 4:
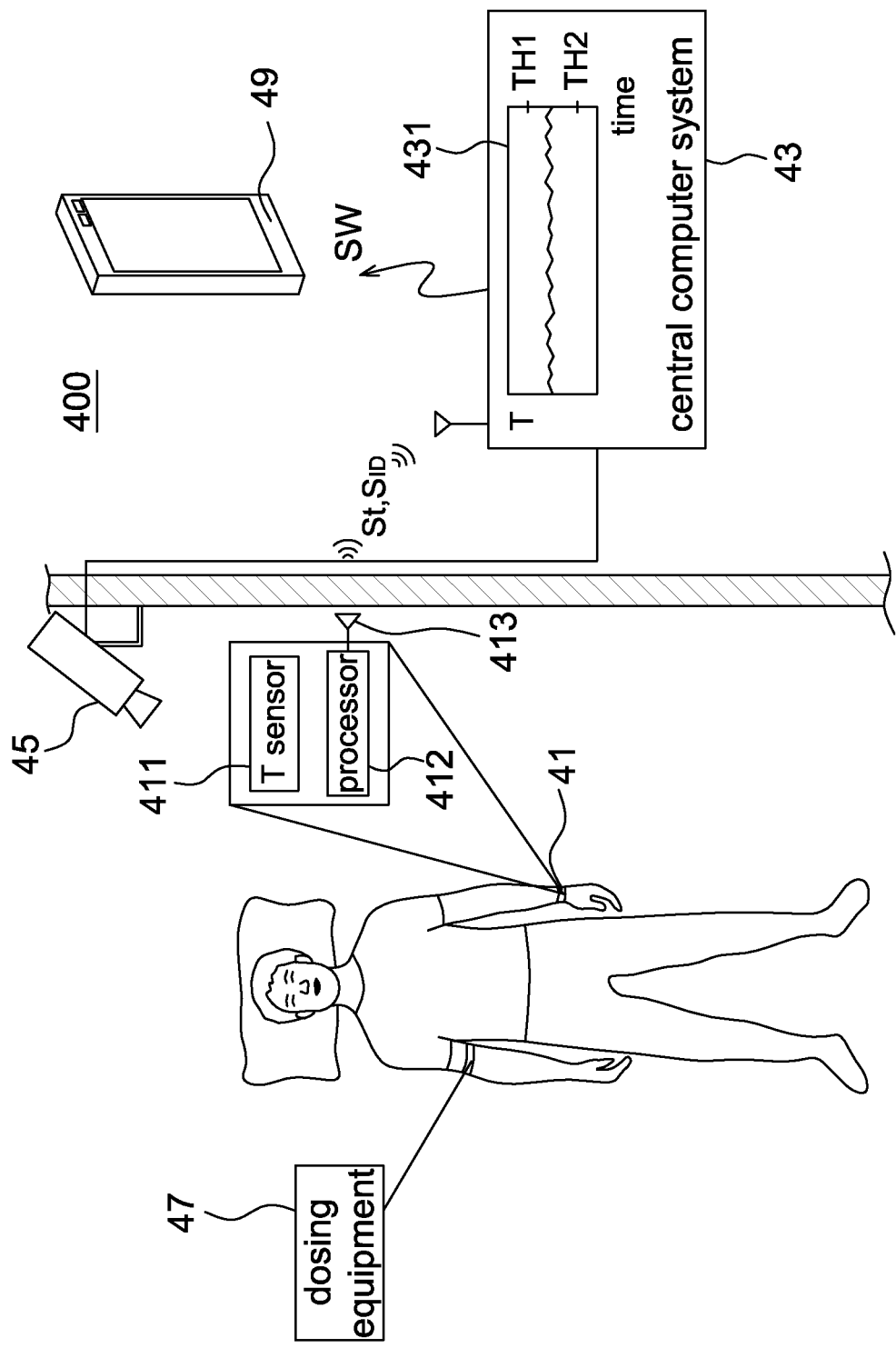
FIG. 4 is a schematic diagram of a medical monitoring system according to a third embodiment of the present disclosure.

Please referring to FIG. 4, it is a schematic diagram of a medical monitoring system 400 according to a third embodiment of the prevent disclosure. The medical monitoring system 400 is applied to a medical institute or a care institute so as to solve the problem caused by the manpower shortage. The medical monitoring system 400 mainly includes a wearable accessory 41 and a central computer system 43 coupled to each other. The wearable accessory 41 is worn on a human body, e.g., FIG. 4 showing on a human arm, but not limited thereto. The wearable accessory 41 is worn on any body part suitable for measuring the body temperature. The central computer system 43 performs a corresponding response, e.g., providing a warning, according to detected results of the wearable accessory 41.

For example, the wearable accessory 41 is a customized accessory, a smart watch, a smart armband, a smart bracelet or the like. The wearable accessory 41 at least includes a thermal sensor (shown as T sensor) 411, a processor 412 and a transmitter 413. The thermal sensor 411 is similar to that in the first and second embodiments for outputting a 2D thermal image, and the processor 412 calculates an average temperature of the 2D thermal image. Besides, in the third embodiment, the thermal sensor 411 includes one sensing unit (e.g., photodiode) and outputs one electrical signal or digital signal at a time to indicate a detected temperature instead of outputting a 2D thermal image. The processor 412 is also a DSP, MCU, CPU, ASIC, GPU or the like.

In the case that the thermal sensor 411 is embedded in other electronic devices not directly contact a user (e.g., the electronic device arranged at the wall or ceiling), the thermal sensor 411 monitors temperature of the whole body of the user. The electronic device provides a warning message St if a temperature difference between the core temperature and limb temperature is larger than a predetermined threshold.

In measuring body temperature, the thermal sensor 411 directly detects a temperature of a skin surface as the body temperature, or detects a temperature difference between the room temperature and the body temperature (i.e. the room temperature and the body temperature being detected simultaneously using identical or different sensors) and obtains the body temperature by subtracting (using the processor 412) the temperature difference from the room temperature.

The thermal sensor 411 is used to detect a body temperature and output an electrical signal or a digital signal to the processor 412. The processor 412 identifies a temperature according to the received signal, and then controls the transmitter 413 (shown by an antenna in FIG. 4) to send a temperature message St associated with the body temperature and a label message SID of the wearable accessory 41 (e.g., the medical monitoring system 400 including multiple wearable accessories 41 each having an individual label) in a wireless manner such as the Bluetooth communication, Zigbee, microwave communication, but not limited to.

In one aspect, the central computer system 43 is arranged at a suitable location capable of receiving the temperature message St and the label message SID, and used to store the received temperature message St onto cloud or in a memory therein. In another aspect, the central computer system 43 includes multiple receivers arranged at different locations to receive the temperature message St and the label message SID from different patients, and a host of the central computer system 43 is electrically connected to these receivers.

When the received temperature message St indicates that the body temperature exceeds a predetermined range, the central computer system 43 generates a warning message Sw associated with the label message SID, wherein said associated with the label message SID is referred to that the warning message Sw is dedicated to a human body who wears the wearable accessory 41 that sends the label message SID so as to avoid the confusion between patients. In one aspect, the warning message Sw is represented by a lamp or a broadcast. In another aspect, the central computer system 43 further includes a transmitter (not shown) for wirelessly sending the warning message Sw to a portable device 49, which is carried by or assigned to a medical staff.

In one non-limiting aspect, the central computer system 43 further includes a display 431 (e.g., LCD or plasma) for showing a temperature distribution with time of the body temperature to be watched by the medical staff. The display 431 shows or is marked a high temperature threshold TH1 and a low temperature TH2 on the screen thereof. When identifying that the body temperature detected by the thermal sensor 411 exceeds a predetermined range (e.g., higher than TH1 or lower than TH2), the central computer system 43 generates the warning message Sw. The thresholds TH1 and TH2 may be set or adjusted corresponding to different users.

In one non-limiting aspect, the central computer system 43 further includes a camera 45. When identifying that the body temperature exceeds the predetermined range, the central computer system 43 turns on the camera 45 to perform the patient monitoring. In normal time, the camera 45 is turned off to protect the privacy of the patient. Furthermore, images acquired by the camera are selected to be shown on the display 431.

In one non-limiting aspect, the central computer system 43 further includes a dosing equipment 47. When identifying that the body temperature exceeds the predetermined range, the central computer system 43 turns on the dosing equipment to perform the automatic dosing. The operating status of the dosing equipment 47 is selected to be shown on the display 431 if it is included. The display 431 further shows the relationship between the dosage and the variation of body temperature. The central computer system 43 further controls the dosing equipment 47 to stop dosing when the body temperature recovers to be within the predetermined range.

Although in the above embodiment the medical monitoring system 400 is applied to an operation organization, the present disclosure is not limited thereto. The medical monitoring system 400 of the third embodiment is also applicable to a home caring system, and the operation of the central computer system 43 is replaced by a tablet computer, a desktop computer or a notebook computer.

Although the third embodiment is described using a wearable accessory 41, it is only intended to illustrate but not to limit the present disclosure. In other aspects, the wearable accessory 41 is replaced by a monitoring device that is not directly attached to a human body. The thermal sensor 411 detects the body temperature by non-contacting the human body.

Figure 5:
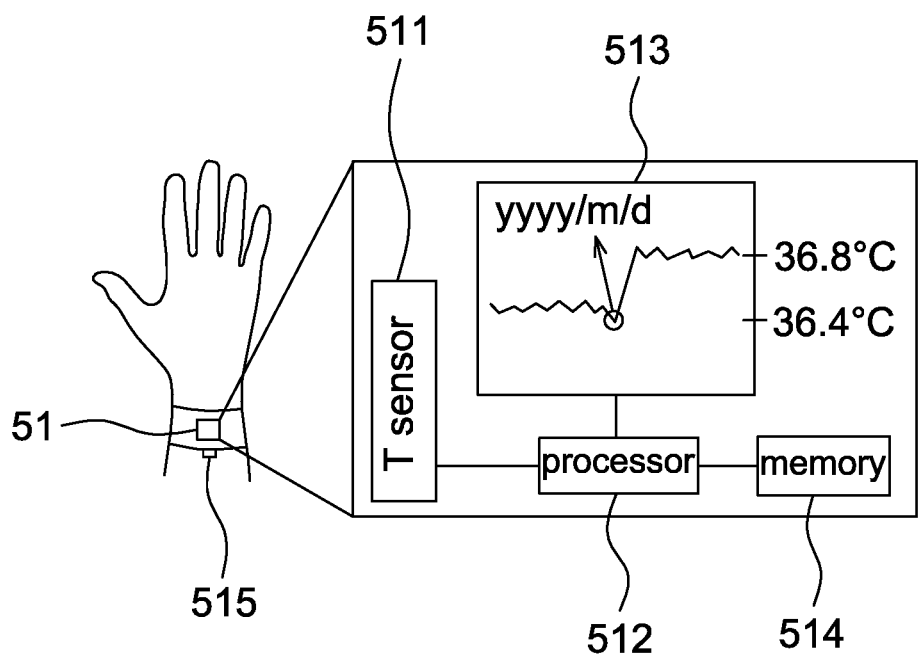
FIG. 5 is a schematic diagram of a body temperature monitoring device according to a fourth embodiment of the present disclosure.

Referring to FIG. 5, it is a schematic diagram of a body temperature monitoring device 500 according to a fourth embodiment of the present disclosure. The body temperature monitoring device 500 includes a wearable accessory 51, a thermal sensor (shown as T sensor) 511, a processor 512, a display 513 and a memory 514. The processor 512 is also a DSP, MCU, CPU, ASIC, GPU or the like.

The wearable accessory 51 is worn on a human body. For example, the wearable accessory 51 is a watch, a bracelet or an armband without particular limitations as long as it is a device attached to and fixed on a skin surface. The thermal sensor 511 is disposed in the wearable accessory 51 and used to detect a basal body temperature (BBT) of a human body, and output an electrical signal or a digital signal to the processor 512. The processor 512 is used to record the BBT every day, and controls the display 513 to give a hint when a temperature variation of the BBT exceeds a temperature variation threshold (e.g., 0.3 to 0.5 degrees which is previously stored in the memory 514).

For example, the processor 512 controls the thermal sensor 511 to measure the BBT at a fixed time of a day every day, e.g., based on a system clock. Or, the body temperature monitoring device 500 further includes a button 515, and when receiving a pressed signal of the button 515, the processor 512 controls the thermal sensor 511 to measure the BBT to be shown on the display 513 and stored in the memory 514 for the long term monitoring.

The display 513 gives various messages using a diagram or numbers, e.g., showing the message including an ovulatory phase or date (e.g., shown by yyyy/m/d), a high temperature interval (e.g., FIG. 5 showing days of BBT at about 36.8 degrees, which is determined according to different users) and a low temperature interval (e.g., FIG. 5 showing days of BBT at about 36.4 degrees, which is determined according to different users) to help the user to know her menstrual period.

Preferably, the BBT is measured when a user wakes up but does not leave the bed yet. Accordingly, to achieve the automatic measurement, the body temperature monitoring device 500 further includes an acceleration detection device (e.g., G-sensor) for detecting whether a user gets out of bed. For example, the acceleration detection device only detects accelerations in two dimensions (e.g., XY axes) before the user gets up, and further detects an acceleration in a third dimension (e.g., Z-axis acceleration) after the user gets up. The processor 512 is further used to identify a wake up time (not leaving bed yet) according to the detected acceleration value of the acceleration detection device, and controls the thermal sensor 511 to automatically detect the BBT at the wake up time. Herein, said detecting an acceleration is referred to that an acceleration value larger than a predetermined threshold is detected.

In one non-limiting aspect, when detecting a user is lying on a bed (e.g., not detecting Z-axis acceleration or other acceleration within a predetermined time interval), the processor 512 controls the thermal sensor 511 to measure a temperature once every a predetermined interval (e.g., one to several minutes). Only the detected temperature before a Z-axis acceleration being detected is taken as the BBT by the processor 512 and stored in the memory 514. To improve the detecting accuracy, if the processor 512 does not detects another Z-axis acceleration within a predetermined time interval after one Z-axis acceleration has been detected, it means that the user only changes a lying posture on the bed and thus the measured temperature temporarily being stored is not considered as the BBT.

In one non-limiting aspect, the temperature monitoring device 500 is further wirelessly coupled to another thermal sensor that includes a wireless transceiver and a processor (e.g., DSP). Said another thermal sensor is arranged near the user or bed. When the temperature monitoring device 500 detects a Z-axis acceleration, a request signal is sent to said another thermal sensor, and the processor of said another thermal sensor recognizes (using hardware and/or software therein to identify a variation of high temperature region in the acquired data) whether the user gets up. If the user gets up, said another thermal sensor sends a response signal to the temperature monitoring device 500 to cause the temperature monitoring device 500 to use a body temperature measured before leaving the bed as the BBT. If the user does not get up, said another thermal sensor does not send a response signal or sends a response signal indicating that it is not necessary to measure a body temperature.

In one non-limiting aspect, when detecting a user shaking the temperature monitoring device 500 in a predetermined pattern (e.g., up-down shaking or left-right shaking for several times), the processor 512 starts to measure a body temperature and records the measured temperature as the BBT.

It is appreciated that numbers mentioned in the above embodiments are only intended to illustrate but not to limit the present disclosure.

It should be mentioned that although the recognition system 100 mentioned above is illustrated to include both the thermal sensor 11 and the image sensor 12, the present disclosure is not limited thereto. In other embodiments, the recognition system 100 includes one of the thermal sensor 11 and the image sensor 12, and receives another signal (e.g., image frame Im or thermal image Ih) from an external sensor via an I/O interface thereof. For example, the recognition system 100 includes the thermal sensor 11 but receives the image frame Im from an external image sensor; or the recognition system 100 includes the image sensor 12 but receives the thermal image Ih from an external thermal sensor.

As mentioned above, the recognition system and monitoring system using only the image sensor has its operational limitation such that a complicated algorithm has to be used to overcome this limitation. Accordingly, the present disclosure further provides a face recognition system, (e.g., FIG. 2A), a gesture recognition system (e.g., FIG. 3A), a medical monitoring system (e.g., FIG. 4) and a body temperature monitoring device (e.g., FIG. 5) that overcome the limitation of a system using only the image sensor by employing a temperature sensor to effectively improve the accuracy of a recognition system and broaden the adaptable scenario of a monitoring system.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A body temperature monitoring device, comprising:
   a wearable accessory, configured to be worn on a human body;
   a thermal sensor, in the wearable accessory, and configured to measure a basal body temperature of the human body;
   an acceleration detection device, in the wearable accessory, and configured to output an acceleration value, which includes an X-axis acceleration, a Y-axis acceleration and a Z-axis acceleration;
   a display, on the wearable accessory, and configured to prompt an ovulatory phase; and
   a processor, in the wearable accessory, and configured to
      identify a wake up time of the human body based on the acceleration value,
      control the thermal sensor to measure the basal body temperature at the wake up time,
      record the basal body temperature measured every day, and
      control the display to prompt the ovulatory phase when a temperature variation of the basal body temperature exceeds a temperature variation threshold,
   wherein a measured temperature by the thermal sensor only before the Z-axis acceleration being detected is taken as the basal body temperature.

2. The body temperature monitoring device as claimed in claim 1, wherein the processor is further configured to control the thermal sensor to automatically measure the basal body temperature at a fixed time of a day based on a system clock.

3. The body temperature monitoring device as claimed in claim 1, further comprising a button, wherein the processor is further configured to control the thermal sensor to further measure the basal body temperature when receiving a pressed signal of the button.

4. The body temperature monitoring device as claimed in claim 1, wherein the display is further configured to show a high temperature interval and a low temperature interval of the basal body temperature.

5. The body temperature monitoring device as claimed in claim 1, wherein the processor is further configured to control the thermal sensor to further measure the basal body temperature upon the acceleration value indicating a predetermined shaking pattern.

6. The body temperature monitoring device as claimed in claim 1, wherein the wearable accessory is a watch, a bracelet or an armband.

7. The body temperature monitoring device as claimed in claim 1, wherein when no further Z-axis acceleration is detected within a predetermined time interval after one Z-axis acceleration is detected, the measured temperature is not considered as the basal body temperature.

8. A wearable accessory, comprising:
   a thermal sensor, configured to measure a basal body temperature via a skin surface of a human body;
   an acceleration detection device, configured to output an acceleration value, which includes an X-axis acceleration, a Y-axis acceleration and a Z-axis acceleration; and
   a processor, coupled to the thermal sensor and the acceleration detection device, and configured to
      identify a wake up time of the human body based on the acceleration value,
      control the thermal sensor to measure the basal body temperature at the wake up time,
      record the basal body temperature measured every day, and
      give a hint when a temperature variation of the basal body temperature exceeds a temperature variation threshold,
   wherein a measured temperature by the thermal sensor only before the Z-axis acceleration being detected is taken as the basal body temperature.

9. The wearable accessory as claimed in claim 8, wherein the wearable accessory is a watch, a bracelet or an armband.

10. The wearable accessory as claimed in claim 8, wherein the processor is further configured to control the thermal sensor to automatically measure the basal body temperature at a fixed time of a day.

11. The wearable accessory as claimed in claim 8, wherein the processor is further configured to control the thermal sensor to further measure the basal body temperature when receiving a pressed signal from a button.

12. The wearable accessory as claimed in claim 8, wherein the basal body temperature is shown on a display and recorded in a memory.

13. A wearable accessory, comprising:
   a thermal sensor, configured to measure a basal body temperature via a skin surface of a user when the user wakes up every day;
   a display;
   an acceleration detection device, configured to output an acceleration value, which includes an X-axis acceleration, a Y-axis acceleration and a Z-axis acceleration; and
   a processor, coupled to the thermal sensor, the display and the acceleration detection device, and configured to
      identify a wake up time of the user every day based on the acceleration value,
      control the thermal sensor to measure the basal body temperature at the wake up time every day, and
      control the display to give a hint when a temperature variation of the basal body temperature measured every day exceeds a temperature variation threshold,
   wherein a measured temperature by the thermal sensor only before the Z-axis acceleration being detected is taken as the basal body temperature.

14. The wearable accessory as claimed in claim 13, wherein the wearable accessory is a watch, a bracelet or an armband.

15. The wearable accessory as claimed in claim 13, wherein the temperature variation threshold is between 0.3 to 0.5 degrees.

16. The wearable accessory as claimed in claim 13, wherein the processor is further configured to control the thermal sensor to further measure the basal body temperature upon the acceleration value indicating a predetermined shaking pattern.

* * * * *